(12) United States Patent
Kipp et al.

(10) Patent No.: US 8,183,233 B2
(45) Date of Patent: May 22, 2012

(54) STABLE PHARMACEUTICAL FORMULATIONS

(75) Inventors: James E. Kipp, Wauconda, IL (US); Joseph Chung Tak Wong, Long Grove, IL (US); Lakshmy Nair, Vernon Hills, IL (US); Reagan Miller, Wildwood, IL (US); Barrett E. Rabinow, Skokie, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 87 days.

(21) Appl. No.: 12/437,679

(22) Filed: May 8, 2009

(65) Prior Publication Data
US 2009/0286764 A1     Nov. 19, 2009

Related U.S. Application Data

(60) Provisional application No. 61/053,301, filed on May 15, 2008.

(51) Int. Cl.
*A01N 43/00* (2006.01)
*A01N 43/16* (2006.01)
*A61K 31/397* (2006.01)
*A61K 31/407* (2006.01)
*A61K 31/35* (2006.01)

(52) U.S. Cl. ............. 514/210.09; 514/451; 514/453; 514/460

(58) Field of Classification Search ............ 514/210.09, 514/451, 453, 460
See application file for complete search history.

(56) References Cited

U.S. PATENT DOCUMENTS

| | | | |
|---|---|---|---|
| 2,908,614 A | 10/1959 | Muggleton et al. | |
| 4,727,064 A * | 2/1988 | Pitha | 514/58 |
| 4,883,785 A * | 11/1989 | Chow et al. | 514/31 |
| 5,472,954 A * | 12/1995 | Loftsson | 514/58 |
| 6,492,382 B1 * | 12/2002 | Bjore et al. | 514/300 |
| 7,094,601 B2 | 8/2006 | Toner et al. | |
| 2003/0138403 A1 | 7/2003 | Drustrup | |

FOREIGN PATENT DOCUMENTS

| | | |
|---|---|---|
| EP | 0410207 | 1/1991 |
| WO | WO 0051564 | 9/2000 |
| WO | WO 2004032902 | 4/2004 |
| WO | WO 2007133711 | 11/2007 |
| WO | WO 2008070721 | 6/2008 |
| WO | WO 2008101175 | 8/2008 |

OTHER PUBLICATIONS

Mendez et al. 2008, Thermal and alkaline stability of meropenem: degradation products and cytotoxicity. International Journal of Pharmaceutics, vol. 350, pp. 95-102.*
Pop et al. "Solubilization and stabilization of a benzylpenicillin chemical delivery system by 2-hydroxypropyl-b-cyclodextrin." Pharmaceutical Research, 1991, vol. 8(8), pp. 1044-1049.*
Ressing, M. E., et al, "The Influence of Sucrose Dextran and Hydroxypropyl-Beta-Cyclodextrin as Lyoprotectants for a Freeze-Dried Mouse IGG2a Monoclonal Antibody (MN12)," Pharmaceutical Research, Jan. 1, 1992, vol. 9, No. 2, pp. 266-270.
International Search Report for International Application No. PCT/US2009/038325 mailed Aug. 25, 2009.
Written Opinion for International Application No. PCT/US2009/038325 mailed Aug. 25, 2009.
International Preliminary Report on Patentability for Appl. No. PCT/US2009/043295 dated Aug. 19, 2010, 12 pages.

* cited by examiner

*Primary Examiner* — Sreeni Padmanabhan
*Assistant Examiner* — Kara R McMillian
(74) *Attorney, Agent, or Firm* — K&L Gates LLP

(57) ABSTRACT

Stable pharmaceutical formulations and methods of making same are provided. In a general embodiment, the present disclosure provides a method of making a stable pharmaceutical formulation comprising adding one or more vitrifying additives to an aqueous pharmaceutical solution to raise the glass transition temperature of the aqueous pharmaceutical solution. The aqueous pharmaceutical solution can be cooled to a temperature of about −50° C. to about −10° C. The vitrifying additive enhances the formation of a glass or amorphous solid of the aqueous pharmaceutical solution at cryogenic temperatures (−50 to −10° C.), and the pharmaceutical formulation can be thawed to liquid form and administered to a mammalian subject.

12 Claims, 14 Drawing Sheets

| Substituent name<br>R = H or | Formula<br>R = H or | Abbreviated designation |
|---|---|---|
| 2-hydroxypropyl-β-CD | $CH_2CH(OH)CH_3$ | HP-β-CD |
| carboxymethyl-β-CD | $CH_2COOH$ | CM-β-CD |
| sulfobutylether-β-CD | $CH_2CH_2CH_2CH_2SO_3Na$ | SBE-β-CD |
| β-CD sulfate, sodium | $SO_3Na$ | |
| randomly methylated β-CD | $CH_3$ | RM-β-CD |

| Carbapenem | R₁ | R₂ | R₃ | R₄ | R₅ |
|---|---|---|---|---|---|
| imipenem | CH(OH)CH₃ (H₃C-CH(OH)-) | H | H | H | –S–CH₂CH₂–N=CH–NH₂ |
| meropenem | CH(OH)CH₃ | H | CH₃ | H | –S–(pyrrolidin-3-yl)–C(=O)N(CH₃)₂ (2-carboxamide) |
| ertapenem | CH(OH)CH₃ | H | CH₃ | H | –S–(pyrrolidin-3-yl)–C(=O)NH–C₆H₄–COOH (meta) |
| doripenem | CH(OH)CH₃ | H | CH₃ | H | –S–(pyrrolidin-3-yl)–CH₂–NHSO₂NH₂ |
| panipenem | CH(OH)CH₃ | H | H | H | –S–(pyrrolidin-3-yl)–N=C(CH₃)–NH (acetimidoyl) |

STABLE PHARMACEUTICAL FORMULATIONS

CROSS-REFERENCE TO RELATED APPLICATIONS

This application claims the benefit of U.S. Provisional Patent Application Ser. No. 61/053,301 filed May 15, 2008, the entire disclosure of which is expressly incorporated herein by reference.

BACKGROUND

The present disclosure relates generally to pharmaceutical formulations. More specifically, the present disclosure relates to stable pharmaceutical formulations and methods of making the stable pharmaceutical formulations.

The use of freezing in the preservation of pharmaceutical agents is known. One example of a frozen pharmaceutical agent is ceftriaxone sodium, which is stable for at least 18 months if stored at or below −20° C. The advantage of a frozen pharmaceutical, compared to a lyophilized or powdered drug for reconstitution, lies in its ease of use. The frozen formulation can be thawed and administered as is to the patient without need for further dilution. This also reduces the potential for medication errors and contamination due to manipulation by the clinician. Nonetheless, for some very unstable drugs, freezing a drug solution can cause degradation of the drug. This is particularly the case with beta-lactam antibiotics such as ampicillin and amoxicillin, carbapenems such as imipenem and meropenem, and large molecular biologics such as some monoclonal antibodies and blood factors. In many cases, this instability arises from high concentration of drug in the unfrozen liquid remaining between ice crystals, and shifts in pH, ionic strength, dielectric strength and other physical properties of this unfrozen liquid.

SUMMARY

The present disclosure is directed to stable pharmaceutical formulations and methods of making the stable pharmaceutical formulations. In a general embodiment, the present disclosure provides a method of stabilizing a pharmaceutical agent. The method comprises combining a therapeutically effective amount of a pharmaceutical agent with water; preferably providing a drug concentration of 0.1 to 100 mg/mL, and one or more vitrifying additives to form an aqueous pharmaceutical solution. The vitrifying additive is present in an amount (for example about 1 to about 30%) effective to enhance the formation of an amorphous solid of the aqueous pharmaceutical solution when the aqueous pharmaceutical solution is cooled to a temperature below a glass transition temperature of the aqueous pharmaceutical solution. The method also comprises cooling the aqueous pharmaceutical solution to a temperature of about −50° C. to about −10° C. to form the amorphous solid, which is the pharmaceutical agent as a stable pharmaceutical formulation.

In an embodiment, the method further comprises aseptically filling the aqueous pharmaceutical solution in a container before cooling. The cooled aqueous pharmaceutical solution can be stored at a temperature of about −10° C. to about −50° C. for a period of at least about three months.

In an embodiment, the aqueous pharmaceutical solution exhibits less than about ten percent degradation after storing. The method can further comprise thawing the aqueous pharmaceutical solution and administering the thawed aqueous pharmaceutical solution to a patient.

In an embodiment, the vitrifying additive is one more polyalcohols, polysaccharides, monosaccharides, disaccharides, trisaccharides, aminosugars, amino derivatives of saccharides, or a combination thereof. The polyalcohol can be, but is not limited to, polyethylene glycol, poloxamers, mannitol, sorbitol, or a combination thereof. The disaccharide can be, but is not limited to, sucrose, trehalose, lactose, or a combination thereof. The trisaccharide can be, but is not limited to, raffinose.

In an embodiment, the polysaccharide can be dextran, cyclodextrin, or a combination thereof. For example, the vitrifying additive can be 2-hydroxypropyl-beta-cyclodextrin. The vitrifying additive can also be a dextran with an average molecular weight of about 1,000 to 70,000, for example about 40,000.

In an embodiment, the pharmaceutical agent is one or more antibiotics, antifungal agents, monoclonal antibodies, plasma proteins, or a combination thereof. The pharmaceutical agent can also be one that is unstable in aqueous solution at room temperature. The antibiotic can be one or more trimethoprims, polymyxin B sulfate, beta-lactams, monobactams, oxazolidinones, macrolides, ketolides, tetracyclines, streptogramins, one or more salts of any of the above, or a combination thereof. The beta-lactams can be cephalosporins, penicillins, thienamycins, carbapenems, penems, cephems, trinems, one or more salts of any of the above, or a combination thereof. The antifungal agent can be an echinocandin antifungal, caspoflngin or a salt thereof.

In another embodiment, the present disclosure provides a method of making a shelf-stable pharmaceutical agent. The method comprises combining a pharmaceutical agent with water and at least one vitrifying additive to form an aqueous pharmaceutical solution. The vitrifying additive is present in an amount effective to give the pharmaceutical agent a shelf-life of at least 3 months, for example at least 6 months. The aqueous pharmaceutical solution is then cooled to a temperature of about −50° C. to about −10° C. to form the amorphous solid of the aqueous pharmaceutical solution.

In an embodiment, the shelf-stable pharmaceutical agent has a shelf-life of least 3 months. In another embodiment, the shelf-stable pharmaceutical agent has a shelf-life of least 6 months.

In an alternative embodiment, the present disclosure provides a pharmaceutical formulation comprising an aqueous pharmaceutical solution comprising water and a pharmaceutical agent that is unstable in aqueous solution at room temperature (15-30° C.) or refrigerated storage (0-15° C.), and one or more vitrifying additives. The vitrifying additive is present in an amount effective to enhance the formation of an amorphous solid of the aqueous pharmaceutical solution when the aqueous pharmaceutical solution is cooled to a temperature below a glass transition temperature of the aqueous pharmaceutical solution. The pharmaceutical formulation can be frozen.

An advantage of the present disclosure is to provide improved stable pharmaceutical formulations.

Another advantage of the present disclosure is to improved frozen pharmaceutical formulations.

Yet another advantage of the present disclosure is to provide an improved method for making stable pharmaceutical formulations.

Still another advantage of the present disclosure is to provide an improved method for making pharmaceutical formulations having a long shelf-life.

Additional features and advantages are described herein, and will be apparent from the following Detailed Description and the figures.

DETAILED DESCRIPTION

Figure 1:
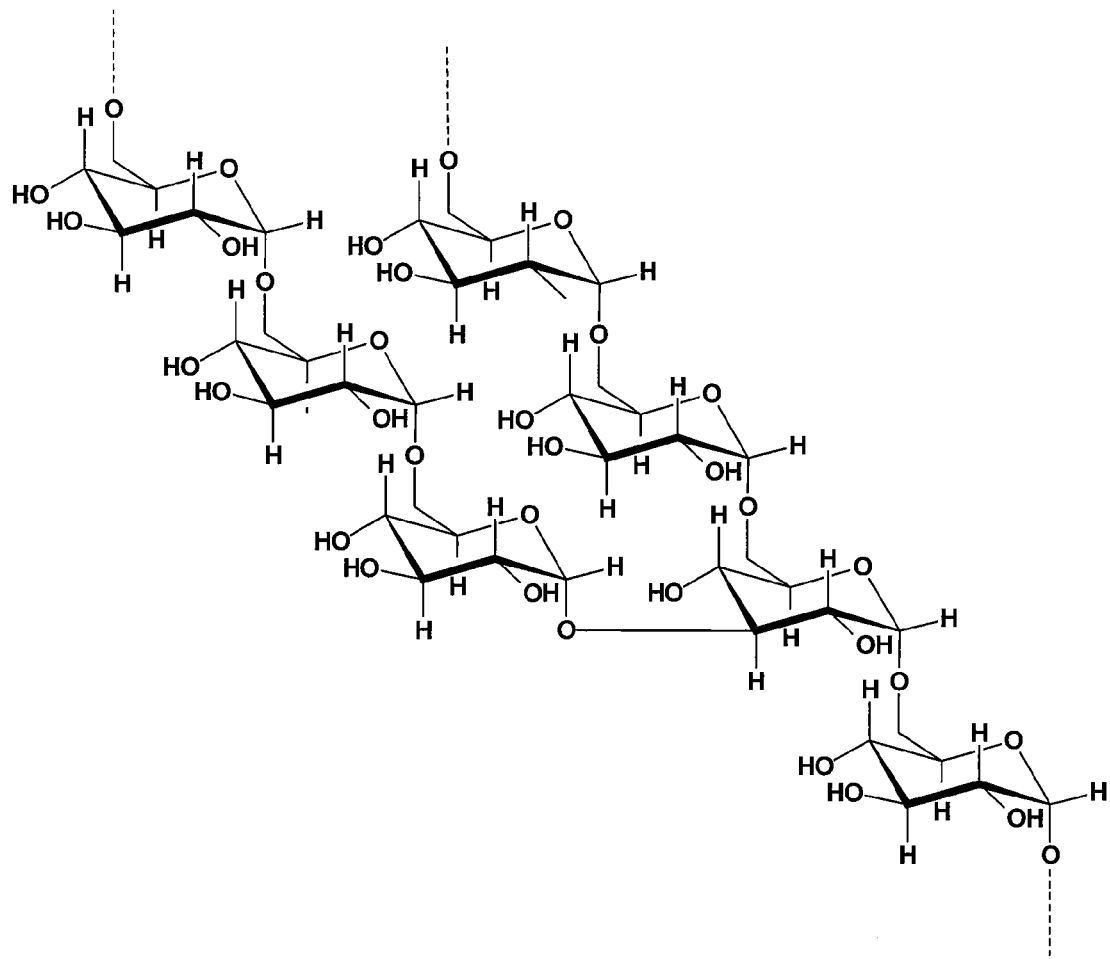
FIG. 1 illustrates the structure of dextrans. Dotted lines indicate continuations of polymer chain.

The present disclosure is directed to stable pharmaceutical formulations and methods of making the stable pharmaceutical formulations. In a general embodiment, one or more vitrifying additives are added to an aqueous pharmaceutical solution. The aqueous pharmaceutical solution can be cooled to a temperature of about −50° C. to about −10° C. Inclusion of the one or more vitrifying or "glass-forming" additives increases the stability of the pharmaceutical agent, for example, in a frozen form.

Non-limiting examples of suitable pharmaceutical agents useful in embodiments of the present disclosure include small molecule drugs such as beta-lactam antibiotics, macrocyclic antibiotics, macrocyclic antifungals, and biologics such as monoclonal antibodies and blood factors such as antihemophilia factor VIII. Preferred beta-lactams include highly unstable drugs such as ampicillin, and carbapenems such as imipenem, meropenem, ertapenem, doripenem and panipenem. Preferred macromolecular antibiotics include erythromycin, azithromycin, dalfopristin and quinupristin. The combination of the latter two is provided in the commercial product, SYNERCID® (by Monarch Pharmaceuticals). Preferred macromolecular antibiotics include echinocandins, including but not limited to caspofungin (CANCIDAS®, by Merck), micafungin (MYCAMINE®, by Astellas), and anidulafungin (ERAXIS®, by Pfizer). These pharmaceutical agents will be discussed in more detail below.

It has surprisingly been found that the stability of pharmaceutical agents can be enhanced by freezing a liquid solution of the pharmaceutical agents to form a solid glass or amorphous solid of the pharmaceutical agents. This can be accomplished by combining with the liquid pharmaceutical solutions at least one vitrifying additive in an amount that raises the glass transition temperature of the liquid pharmaceutical solutions, or otherwise enhances the formation of a glass or amorphous solid at cryogenic temperatures (−50° C. to −10° C.). The resultant frozen pharmaceutical solutions can be thawed to liquid form and administered to a mammalian subject. Inclusion of one or more vitrifying additives increases the stability of the pharmaceutical agent beyond that which would have been attained in the absence of the additive under the same storage conditions.

Vitrifying additives that can raise the glass transition temperature above the standard pharmaceutical agent storage temperature may enhance chemical stability of the pharmaceutical agent. Sugars such as trehalose, sucrose, or raffinose, or a high molecular weight polysaccharide such as dextran can be used as vitrifying agents that effectively raise the glass transition temperature.

As used herein, the term "shelf-life" is defined as the period from the time of manufacture within which 10% drug loss occurs. The inclusion of one or more vitrifying additives increases the shelf-life of the pharmaceutical formulation beyond that which would have been attained in the absence of the additive to the pharmaceutical formulation under the same storage conditions. For example, these vitrifying additives may be used in combination with storage temperatures from about −50° C. to about −10° C. to achieve desired shelf lives of the pharmaceutical agent in the frozen state.

In an embodiment, the vitrifying additive is a polyalcohol, monosaccharide, disaccharide, polysaccharide, aminosugar, aminopolysaccharide, or a combination thereof. Non-limiting examples of polyalcohols include polyethylene glycol, mannitol and sorbitol. Glucose and fructose are examples of monosaccharides. Non-limiting examples of disaccharides are sucrose, trehalose and lactose. Non-limiting examples of polysaccharides include raffinose (a trisaccharide), maltotetraose, dextran, and cyclodextrins such as alpha- or beta-cyclodextrins and their derivatives. Pharmaceutical-grade dextrans include Dextran 40 (MW=40,000), Dextran 1 (MW=1,000), and Dextran 70 (MW=70,000). Dextran solutions are used as plasma expanders. Cyclodextrins that are in prevalent pharmaceutical use include alpha-cyclodextrin, sulfobutylether(7)-beta-cyclodextrin (CAPTISOL®, manufactured by Cydex, Inc.), and 2-hydroxypropyl-beta-cyclodextrin. Sulfobutylether(7)-beta-cyclodextrin is used in several pharmaceutical products such as voriconazole (VFEND®, by Pfizer) and ziprasidone HCl (GEODON®, by Pfizer). 2-Hydroxypropyl-beta-cyclodextrin is used in itraconazole for intravenous injection (SPORANOX® IV, by Janssen Pharmacetica). An example of an aminosugar is N-methylglucamine.

Dextrans are high molecular weight polysaccharides that are cross linked by α-1,6 glycosidic linkages and crosslinked at the C-3 hydroxy groups. FIG. 1 illustrates the structure of dextrans. Dextran 40 has an average molecular weight of 40,000 (range 10,000 to 90,000) and is used pharmaceutically as a plasma-volume expander. Therapeutic examples include (1) the adjunctive treatment of shock or impending shock due to hemorrhage, burns, surgery or other trauma, (2) use as a priming fluid, either as the sole primer or as an additive, in pump oxygenators during extracorporeal circulation, (3) the treatment of deep venous thrombosis ("DVT"), and (4) prophylaxis of pulmonary embolism ("PE") and DVT in patients undergoing procedures associated with a high incidence of thromboembolic complications, such as hip surgery.

Pharmaceutical agents that are normally unstable in solution above freezing can be lyophilized (i.e. freeze-dried) if they are not damaged by the freezing process. The protection of biological molecules by lyophilization is a subject of considerable practical importance, particularly in the pharmaceutical industry. Much work has been conducted on the use of a wide variety of compounds as cryoprotectants for these types of processes. Saccharides are often used in this capacity and have been found to protect proteins during lyophilizing stresses. They have also been shown to prevent damage to cells during lyophilization. Trehalose, a disaccharide of glucose, has been found to be a highly effective. Simple lyophilization generally occurs in three phases: (a) cooling phase, (b) sublimation (primary drying), (c) desorption (final drying or secondary drying). Often, it is desirable to obtain a glass, below the glass transition, by the end of the cooling phase, prior to water removal by sublimation. Typically, the final temperature reached is well below −20° C., and quite often is lower than −35° C. Embodiments of the present disclosure provide preservation methods that do not dry the material, therefore ambient pressure reduction to remove water and the attendant use of complicated lyophilization apparatuses are not needed.

Embodiments of the present disclosure do not entail the partial or complete dehydration and lyophilization of unstable pharmaceutical agents, but rather the long-term storage of such pharmaceutical agents in an aqueous matrix that is frozen at a high sub-zero temperature (e.g., −20° C.), which enables storage in commercial freezers that are generally found in a hospital setting. Typically, biological tissues are frozen to extreme cryogenic temperatures such as that of liquid nitrogen (−70° C.). Certain frozen aqueous pharmaceutical formulations of the present disclosure have an advantage in that they can be thawed to a liquid state and used as is in a therapeutic drug regimen. In an alternative embodiment, certain frozen formulations of the present disclosure contain concentrated drug solutions that may be diluted with a pharmaceutically acceptable diluent after thawing.

Figure 2:
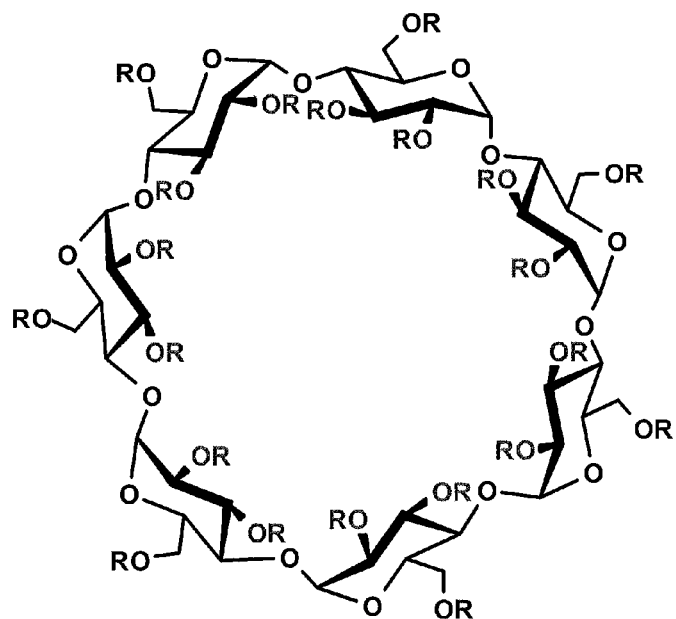
FIG. 2 illustrates the structure of beta-cyclodextrin and some of its derivatives (see R groups).

Cyclodextrins are polysaccharides in which the sugar subunits are concatenated in a ring. FIG. 2 illustrates the structure of beta-cyclodextrin and some of its derivatives (see R groups). Cyclodextrins are nearly always used in the pharmaceutical art and elsewhere to enhance solubility. Far less common is their use to stabilize drugs in solution. Solubility and stability enhancement is due to the formation of inclusion complexes, in which a poorly soluble, hydrophobic drug is partially encapsulated on a molecular level by the cyclodextrin molecule, which possesses a hydrophobic cavity. Because the outside surface of the cyclodextrin can interact with water molecules, aqueous solubility is usually improved. By a similar encapsulation mechanism, reaction of a drug molecule with water may be impeded, although this stabilization is not usually dramatic because water molecules can still diffuse into the open cyclodextrin cavity to interact with the drug.

It has surprisingly been found that Dextran 40 and 2-hydroxypropyl-beta-cyclodextrin are excellent vitrifying agents for the enhancement of chemical stability of drugs in the frozen state at −25 to −20° C. A high-degree of stabilization by 2-hydroxypropyl beta-cyclodextrin was not expected because generally the glass transition temperature ("Tg") of polysaccharides is proportional to their molecular weight, and 2-hydroxypropyl beta-cyclodextrin has a low molecular weight (approximately 1400) relative to the high molecular weight dextrans, such as Dextran 40.

The stable pharmaceutical formulations in embodiments of the present disclosure can allow for the use of freezers at conventional sub-zero temperature (−20 to −25° C.) rather than using ultra-cold (−80 to −50° C.) or cryogenic (−180 to −80° C.) storage in the clinical setting. Storage at higher temperature saves energy and cost, as compared to lower cryogenic temperatures. Many hospital freezers are set at −20 to −25° C. in order to accommodate commercially available pharmaceutical products, such as frozen premixed infusion products, and therefore current hospital infrastructures and protocols can be followed. The stable pharmaceutical formulations can be thawed and used directly as is. In contrast, in the case of lyophilized products, the powder must be reconstituted with an aqueous diluent that is acceptable for injection. This reconstitution procedure must be conducted under aseptic conditions, usually under a laminar-flow hood.

As previously discussed, there are many pharmaceutical agents that are highly unstable in solution and would benefit from the addition of glass-transition modifiers as covered by embodiments of the present disclosure. Such pharmaceutical agents include, but are not limited to, beta-lactams such as carbapenems, some penicillins such as ampicillin, other antibiotics such as SYNERCID® (quinupristin-dalfopristin), antifungal agents such as caspofungin (CANCIDAS®, by Merck), micafungin (MYCAMINE®, by Astellas), and anidulafungin (ERAXIS®, by Pfizer) and biologics such as monoclonal antibodies, and blood factors such as antihemophilia factor VIII.

Figure 3:
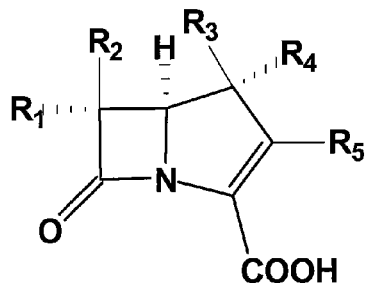
FIG. 3 illustrates the carbapenem structure (see R groups for identification of different carbapenems).

The instability of carbapenems having the structure shown below arises from ring strain created by the carbon-carbon double bond that is endocyclic to the 5-membered ring (FIG. 3 shows various R groups).

This ring system is more strained than that of other beta-lactams such as various penicillins and cephalosporins. The rate of hydrolytic cleavage of the beta-lactam ring of the carbapenem is thereby enhanced. Meropenem (MERREM®, by AstraZeneca, see FIG. 3) is one example of a beta-lactam antibiotic of the carbapenem class. Other carbapenems include imipenem, ertapenem, panipenem, and doripenem.

The stability and degradation kinetics of meropenem have been studied. Meropenem is predicted to have a shelf-life (t90) of about 0.5 day at 0° C. Extrapolated to −25° C., the predicted shelf-life is less than one month. Meropenem also polymerizes at higher drug concentration by a second-order mechanism. If one requires a meropenem formulation that is ready-to-use, there is value in being able to stabilize these compounds in frozen aqueous media.

Another class of drugs used in embodiments of this disclosure is the echinocandin class of antifungals, as represented by caspofungin (CANCIDAS®, by Merck), micafungin (MYCAMINE®, Astellas) and anidulafungin (ERAXIS®, by Pfizer). Caspofungin acetate (CANCIDAS®, by Merck) is shown below:

Caspofungin is unstable in liquid form. It is available commercially as a lyophilized powder for reconstitution. Prior to use, the powder is dissolved in 10.5 mL of diluent (e.g., 0.9% Sodium Chloride Injection) to prepare a concentrate that is only stable for up to one hour at ≦25° C. Ten mL of this concentrate is aseptically transferred to an intravenous ("IV") bag (or bottle) containing 250 mL of infusion diluent (e.g., 0.9% Sodium Chloride Injection). This infusion solution must be used within 24 hours if stored at ≦25° C. (≦77° F.) or within 48 hours if stored refrigerated at 2 to 8° C. (36 to 46° F.) (CANCIDAS® package insert, Merck Inc.). A frozen formulation that is ready-to-use upon thawing to a liquid may only be possible if incorporated into a cryogenic glass. Embodiments of the present disclosure can also provide for the development of a frozen caspofungin formulation that can be thawed and inhaled for the treatment of pulmonary fungal infections. The aerosolization of caspofungin preparations can be done using conventional nebulizers.

Other unstable drugs can be formulated using this embodiment of the present disclosure, and include, without limitation, the following antibiotics: trimethoprims; polymyxin B sulfate; beta-lactams, including, without limitation, cephalosporins, penicillins, thienamycins, carbapenems, penems, cephems, and trinems; oxazolidinones; macrodlides, including without limitation, erythromycins and erythromycin lactobionate; ketolides; tetracyclines, including, without limitation, chlortetracyclines and chlortetracycline hydrochloride; and streptogramins, including, without limitation, pristinomycins such as a combination of the pharmaceutical agents quinupristin and dalfopristin (known commercially as SYNERCID®).

In an alternative embodiment of the present disclosure, a pharmaceutical agent is dissolved in Water for Injection, optionally with an excipient to adjust the osmotic strength of the medium, and optionally with a buffer. Depending on stability of the drug, the solution pH is adjusted to about 3 to 11. After dissolving all ingredients, the solution is filled by an aseptic process into glass or plastic containers. During mixing and filling, the solution may be cooled to retard decomposition of drug. The filled containers are then frozen to a temperature of about −50° C. to about −10° C. Preferred containers include flexible plastic bags intended for packaging of injectable pharmaceutical products.

Such flexible plastic containers may be made of a single polymeric layer or multiple layers bonded together, or co-extruded. These film layers can comprise polymers such as, but not limited to, polyolefins, polyethers, and polyamides (nylon, for example). An example of a flexible plastic container is the GALAXY® container system (Baxter International Inc., Deerfield, Ill.), intended for intravenous drug infusion. The aforementioned formulation may alternatively be aseptically filled into glass or plastic syringes for medical use. The prepared solution, packaged in a container approved for medical application, is then frozen, and distributed to the customer for thawing to a liquid form at a desired concentration and purity for administration to a mammalian subject. The thawed formulation can be administered by parenteral routes that include intravenous, intramuscular, subcutaneous, intrathecal, intracerebral, intraurethral, intradermal, intracardiac and intraosseous.

In another embodiment of this invention, the frozen solution is thawed to a liquid state, in which form it is ready to be administered to a mammalian subject. In another embodiment, the frozen solution is concentrated in pharmaceutical agent and when thawed can be diluted to the desired final concentration for administration. This may be beneficial for the stabilization of some pharmaceutical agents that may otherwise not be stable in the frozen state at the final deliverable concentration, even when in the presence of vitrifying agents that are at a clinically acceptable concentration. However, if the same solution is reduced in volume, the concentration of the vitrifying agent inversely increases. It is known that increasing the concentration of many vitrifying agents will increase the glass transition temperature of the aqueous solution in the frozen state (Angell CA, Liquid fragility and the glass transition in water and aqueous solutions. Chem. Rev. 2002, 102, 2627-2650). This is beneficial in stabilizing the pharmaceutical agent in frozen solution because it can be stored as a concentrate at a temperature well below Tg'.

Another advantage to preparation of a concentrate is the ability to use other vitrifying agents such as monosaccharides or sugar alcohols. An example of a monosaccharide is glucose. An example of a sugar alcohol is mannitol. Another example of a sugar alcohol is sorbitol. The above vitrifying agents would have too low a Tg' (below −20° C.) for stable storage at −20° C. Increasing their concentration would shift Tg' above −20° C.

EXAMPLES

By way of example and not limitation, the following examples illustrate the stable pharmaceutical formulations in accordance with embodiments of the present disclosure. The percentages described herein are weight percentages unless specified otherwise.

Example 1

This experiment was performed to determine the glass transition temperature ("Tg'") of frozen meropenem formulations and simple solutions by differential scanning calorimetry. In order to determine whether there was a correspondence between measured glass transition temperature and drug stability, the glass transition temperatures of simple solutions for vitrifying agents and different formulations of meropenem with added vitrifying agents were measured using a Q1000 differential scanning calorimeter ("DSC") equipped with a refrigerated cooling system (TA Instruments, New Castle, Del.).

Tzero™ sapphire disks were used for second cell resistance and capacitance run in the calibration process. The cell constant and temperature calibration were determined using indium standard. An N2-4000 nitrogen generator (Parker Hannifin, Haverhill, Mass.) provided the purging gas at 20 psi. Each solution sample between 15 to 30 mg of a solution was transferred inside an aluminum DSC pan. An aluminum top was placed on the sample and crimped in place. An empty sample container was used as a reference.

The sample was cooled at a rate of 5° C./min from room temperature to −40° C., held for 3 min for thermal equilibration and heated at a rate of 2° C./min to 10° C. All glass transition temperature values were reported as the midpoint of the transition. The results are shown below in Table 1:

TABLE 1

Tg values of frozen solutions (50 mL final diluted volume) determined by DSC

| # | Solution | Tg (° C.) |
|---|---|---|
| 1 | Meropenem (1.42 g blend with sodium carbonate), 6% hydroxyethylstarch, 0.22% NaCl, pH 7.3 | −28.14 |
| 2 | Meropenem (1.42 blend with sodium carbonate), 10% Dextran 40, 0.22% NaCl, pH 7.3 | −18.01 |
| 3 | Meropenem (1.42 blend with sodium carbonate), 10% Dextran 40, 0.22% NaCl, pH 7.9 | −17.40 |
| 4 | Meropenem (1.42 blend with sodium carbonate), 8% Captisol, 0.22% NaCl, pH 7.3 | −34.16 |
| 5 | Meropenem (1.42 blend with sodium carbonate), 13.3% 2-hydroxypropyl β-cyclodextrin, 0.22% NaCl, pH 7.3 | −20.05 |
| 6 | Control (no added vitrifying agent): Meropenem (1.42 blend with sodium carbonate), 0.22% NaCl, pH 7.3, | <−40 |
| 7 | 15% Dextran 40 | −10.78 |
| 8 | 15% 2-Hydroxypropyl-β-cyclodextrin ("HPBC") | −12.62 |
| 9 | 15% Trehalose | −28.14 |
| 10 | 15% Raffinose | −25.37 |
| 11 | 15% Sucrose | −31.17 |
| 12 | 6% Hetastarch | −13.24 |
| 13 | 8% Captisol | −28.01 |

As seen in Table 1, the absence of a vitrifying agent in the control formulation (#6) led to a glass transition temperature less than −40° C.

Example 2

This experiment was performed to determine the meropenem decomposition in samples stored through 6 months at −25° C. The following formulations were prepared by mixing the ingredients shown below in a refrigerated vessel (2-8° C.). The meropenem trihydrate was received as bulk raw material (meropenem bulk blend) that already contained added sodium carbonate ($Na_2CO_3$). Dissolution of 1.42 g of the blended material in 50 mL of distilled water resulted in a final concentration of 20 mg/mL meropenem and 4.16 mg/mL sodium carbonate.

Formulation 1A:

| Meropenem bulk blend | |
|---|---|
| Meropenem trihydrate | 20 mg/mL (as anhydrous) |
| Sodium carbonate | 4.16 mg/mL |
| Hydroxyethyl starch | 60 mg/mL (6%) | pH adjusted to 7.3 with lactic acid and/or sodium hydroxide.

Formulation 1B:

| Meropenem bulk blend | |
|---|---|
| Meropenem trihydrate | 20 mg/mL (as anhydrous) |
| Sodium carbonate | 4.16 mg/mL |
| Sodium chloride | 0.22 mg/mL |
| Dextran 40 | 100 mg/mL (10%) | pH adjusted to 7.3 with hydrochloric acid and/or sodium hydroxide.

Formulation 1C:

| Meropenem bulk blend | |
|---|---|
| Meropenem trihydrate | 20 mg/mL (as anhydrous) |
| Sodium carbonate | 4.16 mg/mL |
| Sodium chloride | 0.22 mg/mL |
| Dextran 40 | 100 mg/mL (10%) | pH adjusted to 7.9 with hydrochloric acid and/or sodium hydroxide.

Formulation 1D:

| Meropenem bulk blend | |
|---|---|
| Meropenem trihydrate | 20 mg/mL (as anhydrous) |
| Sodium carbonate | 4.16 mg/mL |
| Sodium chloride | 0.22 mg/mL |
| Captisol | 80 mg/mL (8%) | pH adjusted to 7.3 with hydrochloric acid and/or sodium hydroxide.

Formulation 1E:

| Meropenem bulk blend | |
|---|---|
| Meropenem trihydrate | 20 mg/mL (as anhydrous) |
| Sodium carbonate | 4.16 mg/mL |
| Sodium chloride | 0.22 mg/mL |
| 2-hydroxypropyl β-cyclodextrin | 133 mg/mL (13.3%) | pH adjusted to 7.9 with hydrochloric acid and/or sodium hydroxide

Formulation 1F (Control):

| Meropenem bulk blend | |
|---|---|
| Meropenem trihydrate | 20 mg/mL (as anhydrous) |
| Sodium carbonate | 4.16 mg/mL |
| 0.9% Sodium Chloride Injection, USP | QS | pH 7.8 (no adjustment of pH)

Flexible plastic containers (50-mL, BAXTER GALAXY® PL2040) were filled with the above formulations (50-mL fill volume). Units were pulled ("Prefreeze units") and immediately tested for meropenem concentration by high-performance liquid chromatography ("HPLC") (test samples were maintained at 5° C. throughout the assay period. The remaining test units of each formulation were placed in stability chambers at −25° C.

Figure 4:
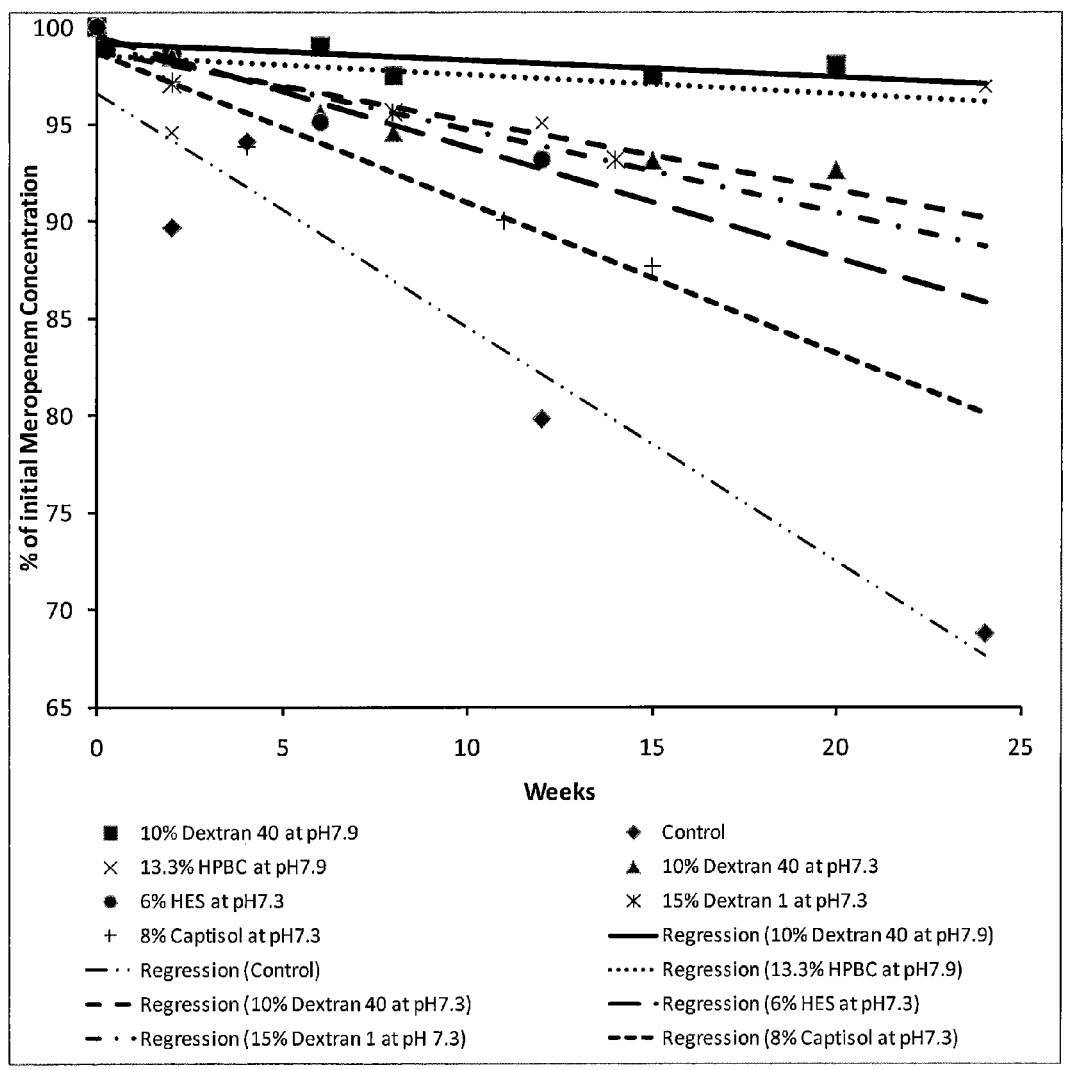
FIG. 4 is a graph showing the concentration of meropenem formulations through intervals up to 6 months at −25° C.
Figure 5A:
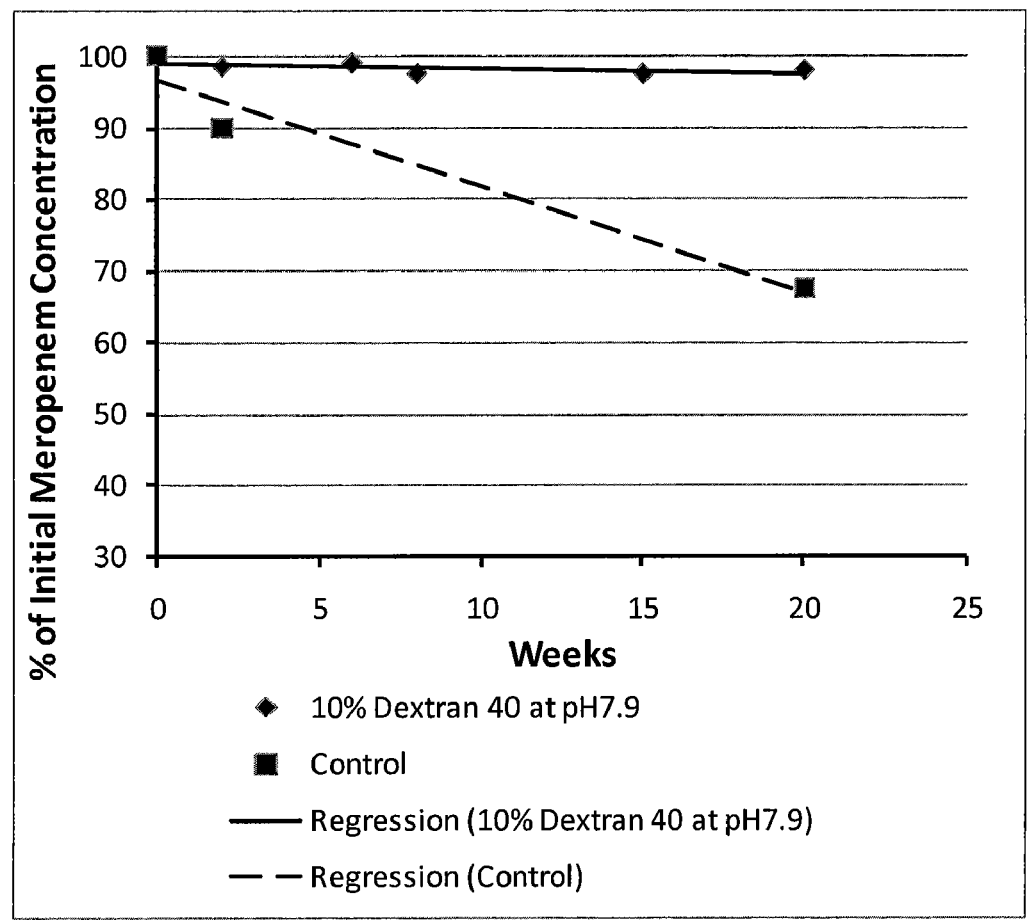
FIG. 5A is a graph showing the concentration of meropenem in 10% Dextran 40, pH 7.9, versus control without 10% Dextran 40 after 20 weeks at −25° C.
Figure 5B:
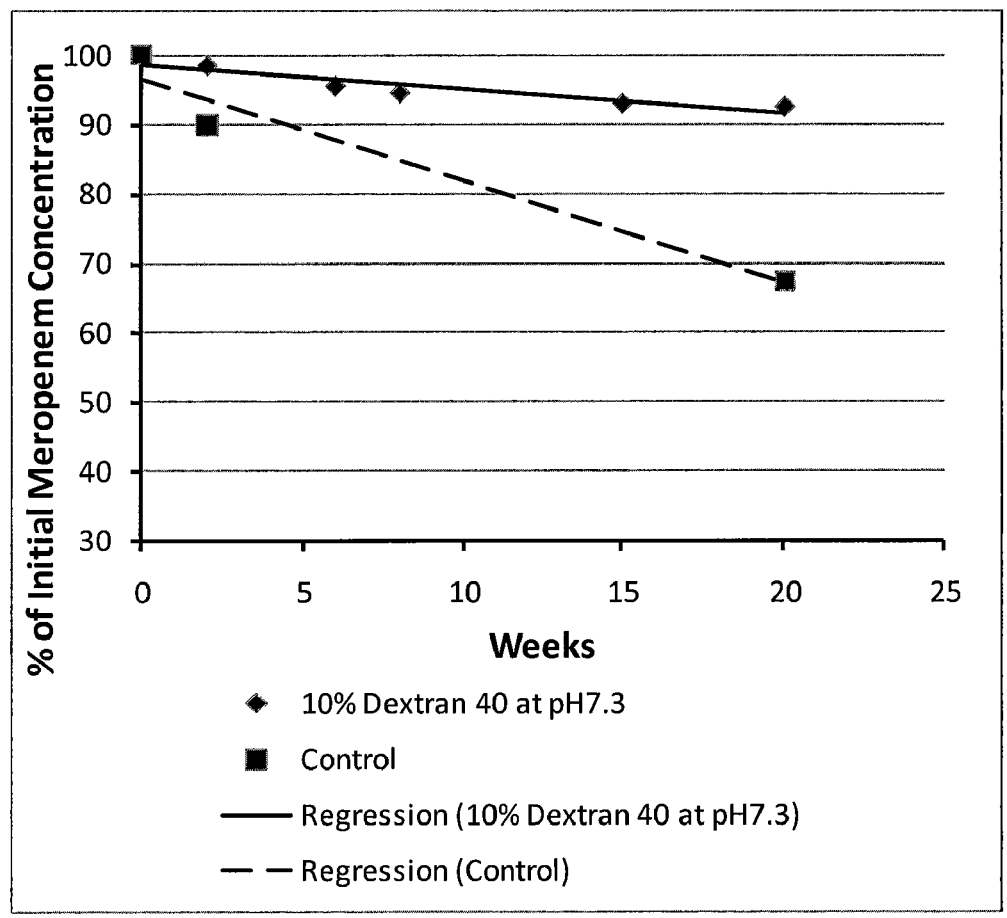
FIG. 5B is a graph showing the concentration of meropenem in 10% Dextran 40, pH 7.3, versus control without 10% Dextran 40 after 20 weeks at −25° C.

After periodic intervals up to approximately 6 months at −25° C., samples were thawed to room temperature and immediately analyzed for meropenem by HPLC. The results are shown in FIG. 4. Samples that contained either Dextran 40 or 2-hydroxypropyl beta-cyclodextrin were the most stable over 6 months at −25° C. FIG. 5A (pH 7.9) and FIG. 5B (pH 7.3) show a comparison between the stability of Formulation 1C (10% Dextran 40) and control samples (Formulation 1F) without Dextran 40, the vitrification additive.

Example 3

This experiment was performed to determine meropenem decomposition in samples stored through 6 months at −20° C. and −25° C., in which combinations of vitrification additives were used. The stability of meropenem formulations was demonstrated with various combinations of 2-hydroxypropyl beta-cyclodextrin, trehalose, mannitol, and sucrose. Samples were stored at −25° C. (FIGS. 6A, 7A, 8A and 9A) and at a higher frozen temperature (−20° C.; FIGS. 6B, 7B, 8B and 9B).

The following formulations were prepared by mixing the ingredients shown below in a refrigerated vessel (2-8° C.). The meropenem trihydrate was received as bulk raw material (meropenem bulk blend) that already contained added sodium carbonate ($Na_2CO_3$). Dissolution of 1.42 g of the blended material in 50 mL of distilled water resulted in a final concentration of 20 mg/mL meropenem and 4.16 mg/mL sodium carbonate.

Formulation 3A: 13% 2-Hydroxypropyl beta-cyclodextrin
    Each 50 mL (0.2 m Nylon Membrane Filtered) in a plastic infusion bag
    Meropenem-R=1.14 g
    Sodium Carbonate, NF=0.21 g
    2-Hydroxypropyl beta-cyclodextrin=6.65 g
    Sterile Water for Injection, USP=QS 50 mL
    pH 7.9 (No pH Adjustment)

Formulation 3B: 9% 2-Hydroxypropyl beta-cyclodextrin+trehalose
    Each 50 mL (0.2 m Nylon Membrane Filtered) in a plastic infusion bag
    Meropenem-R=1.14 g
    Sodium Carbonate, NF=0.21 g
    2-Hydroxypropyl beta-cyclodextrin=4.5 g
    Trehalose=2.59 g
    Sterile Water for Injection, USP=QS 50 mL
    pH 7.9 (No pH Adjustment)

Formulation 3C: 9% 2-Hydroxypropyl beta-cyclodextrin+mannitol
    Each 50 mL (0.2 m Nylon Membrane Filtered) in a plastic infusion bag
    Meropenem-R=1.14 g
    Sodium Carbonate, NF=0.21 g
    2-Hydroxypropyl beta-cyclodextrin=4.5 g
    Mannitol, USP=1.19 g
    Sterile Water for Injection, USP=QS 50 mL
    pH 7.9 (No pH Adjustment)

Formulation 3D: 9% 2-Hydroxypropyl beta-cyclodextrin+sucrose
    Each 50 mL (0.2 m Nylon Membrane Filtered) in a plastic infusion bag
    Meropenem-R=1.14 g
    Sodium Carbonate, NF=0.21 g
    2-Hydroxypropyl beta-cyclodextrin=4.5 g
    Sucrose, USP=2.00 g
    Sterile Water for Injection, USP=QS 50 mL
    pH 7.9 (No pH Adjustment)

Formulation 3E: Control
    Each 50 mL (0.2 m Nylon Membrane Filtered) in a plastic infusion bag
    Meropenem-R=1.14 g
    Sodium Carbonate, NF=0.21 g
    0.9% Sodium Chloride Injection, USP=QS 50 mL
    pH 7.9 (No pH Adjustment)

Figure 6A:
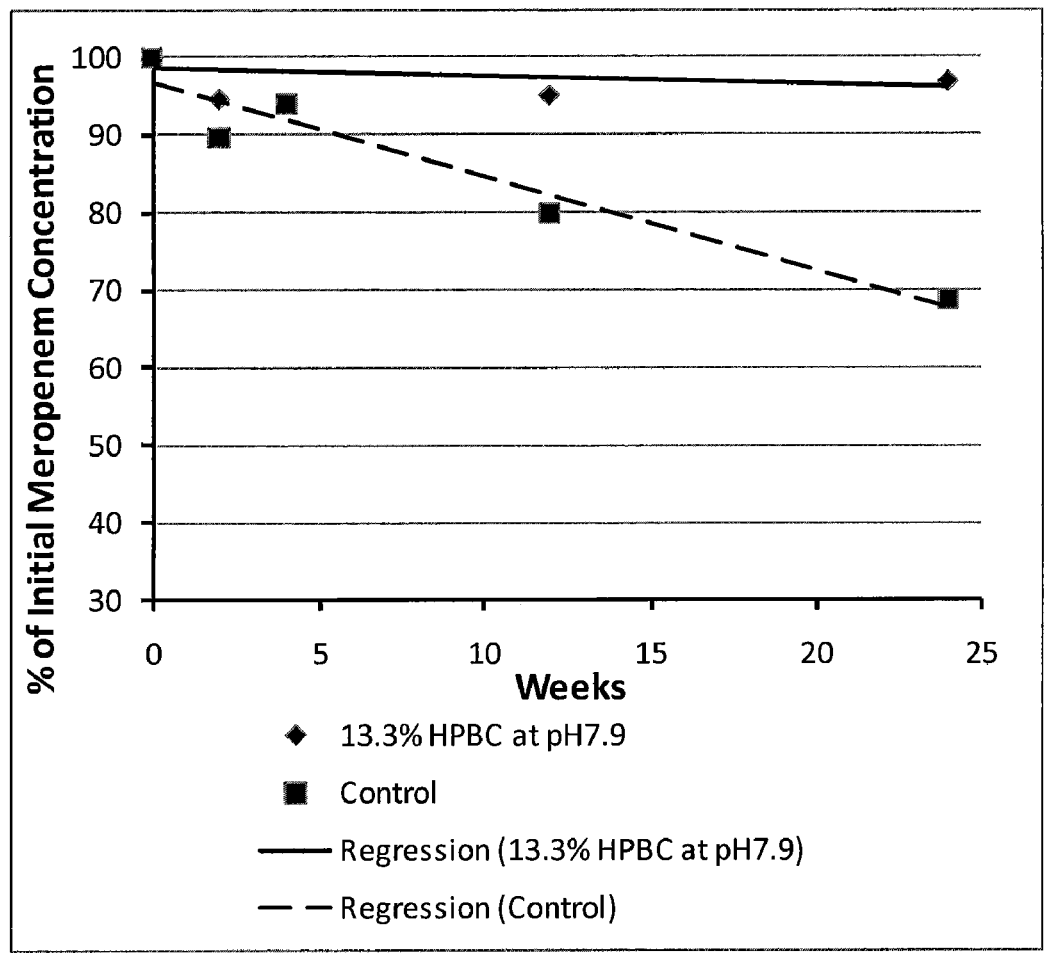
FIG. 6A is a graph showing the percent of initial drug with 13.3% 2-hydroxypropyl beta-cyclodextrin versus storage period (weeks) at −25° C.
Figure 6B:
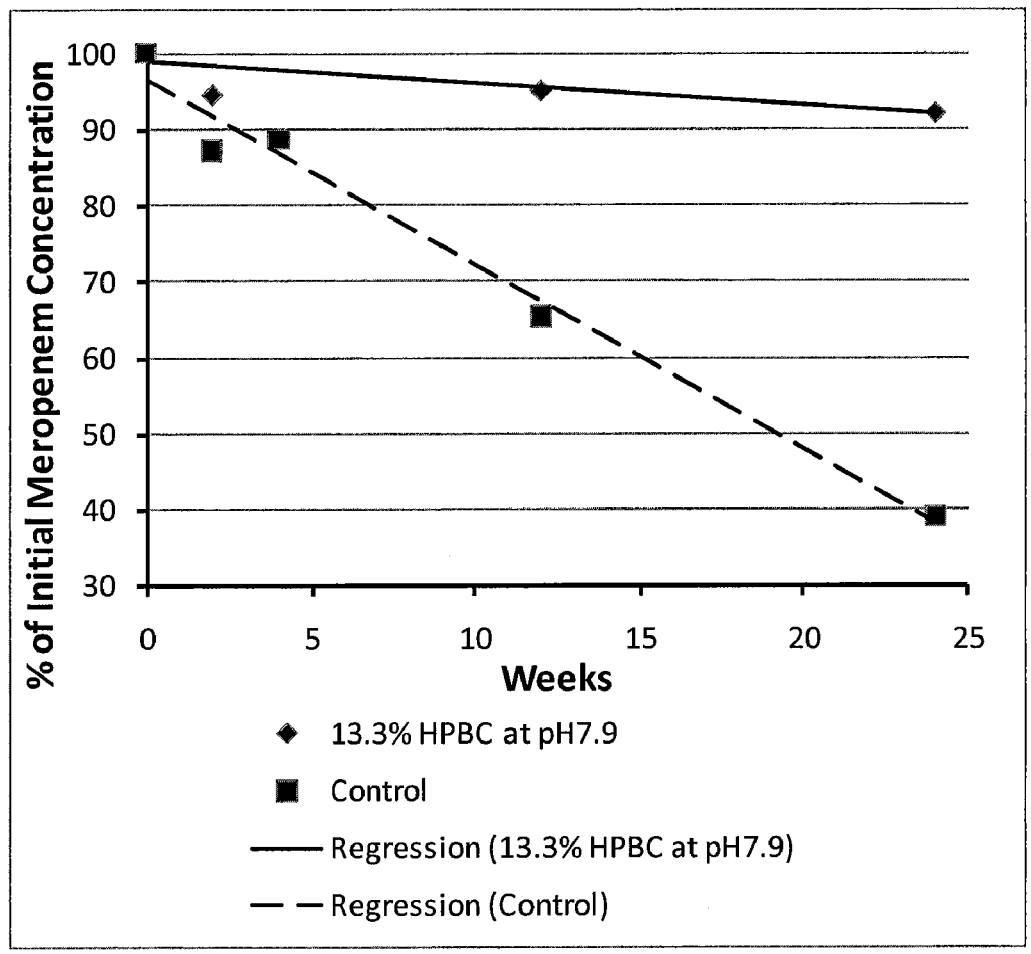
FIG. 6B is a graph showing the percent of initial drug with 13.3% 2-hydroxypropyl beta-cyclodextrin versus storage period (weeks) at −20° C.

Results for Formulation 3A (13% 2-Hydroxypropyl beta-cyclodextrin):
    No significant change in drug concentration occurred through six months at −25° C. (FIG. 6A). The concentration was also maintained above 90% when stored at −20° C. (FIG. 6B).

Figure 7A:
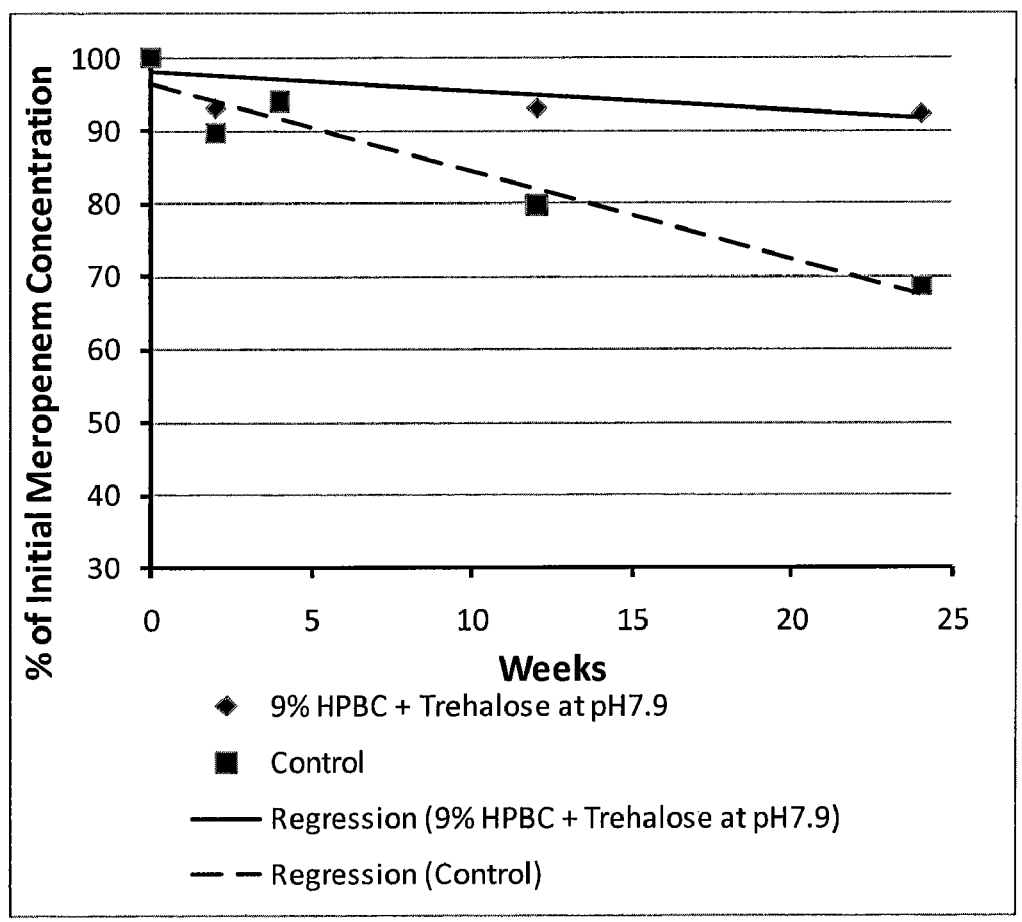
FIG. 7A is a graph showing the percent of initial drug with 9% 2-hydroxypropyl beta-cyclodextrin and trehalose versus storage period (weeks) at −25° C.
Figure 7B:
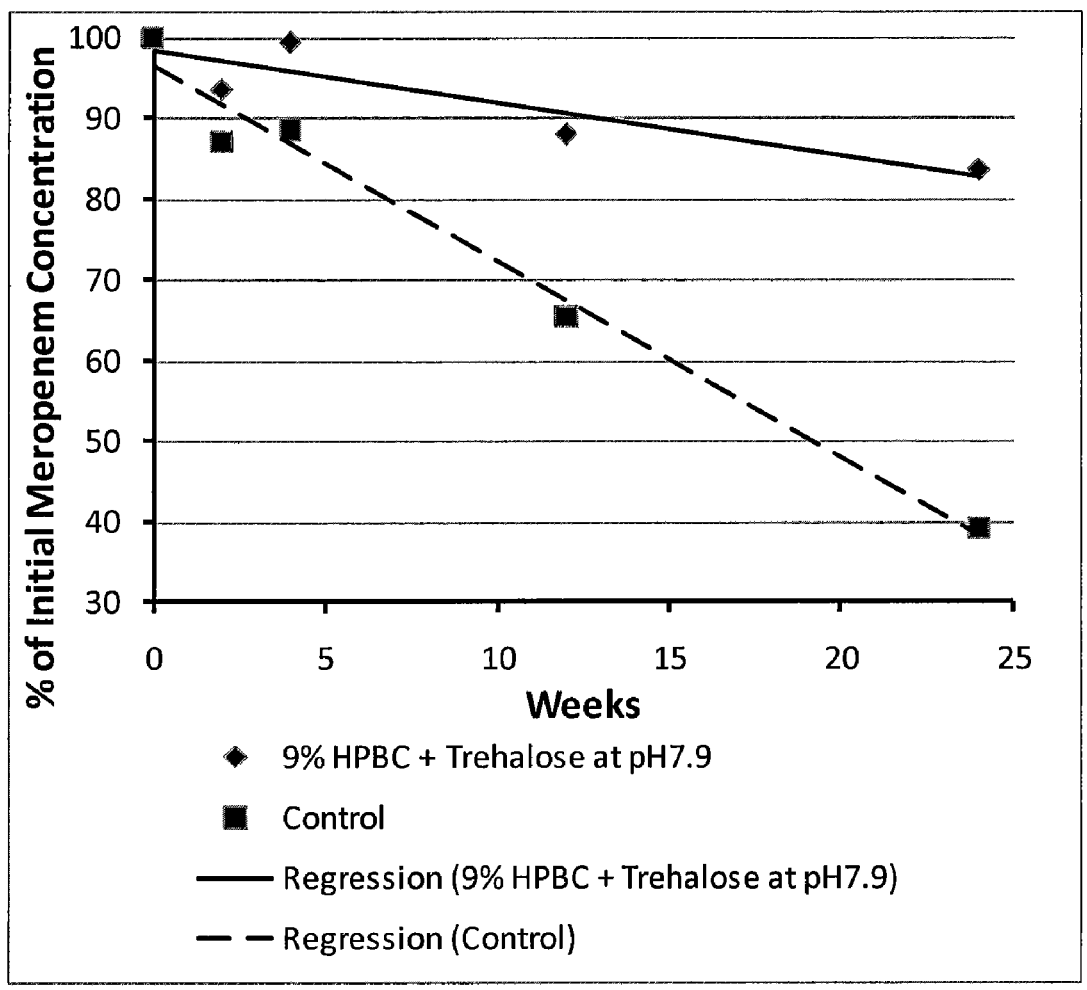
FIG. 7B is a graph showing the percent of initial drug with 9% 2-hydroxypropyl beta-cyclodextrin and trehalose versus storage period (weeks) at −20° C.

Results for Formulation 3B (9% 2-Hydroxypropyl beta-cyclodextrin+trehalose):
    The concentration was also maintained above 90% when stored through 6 months at −25° C. (FIG. 7A).

Figure 8A:
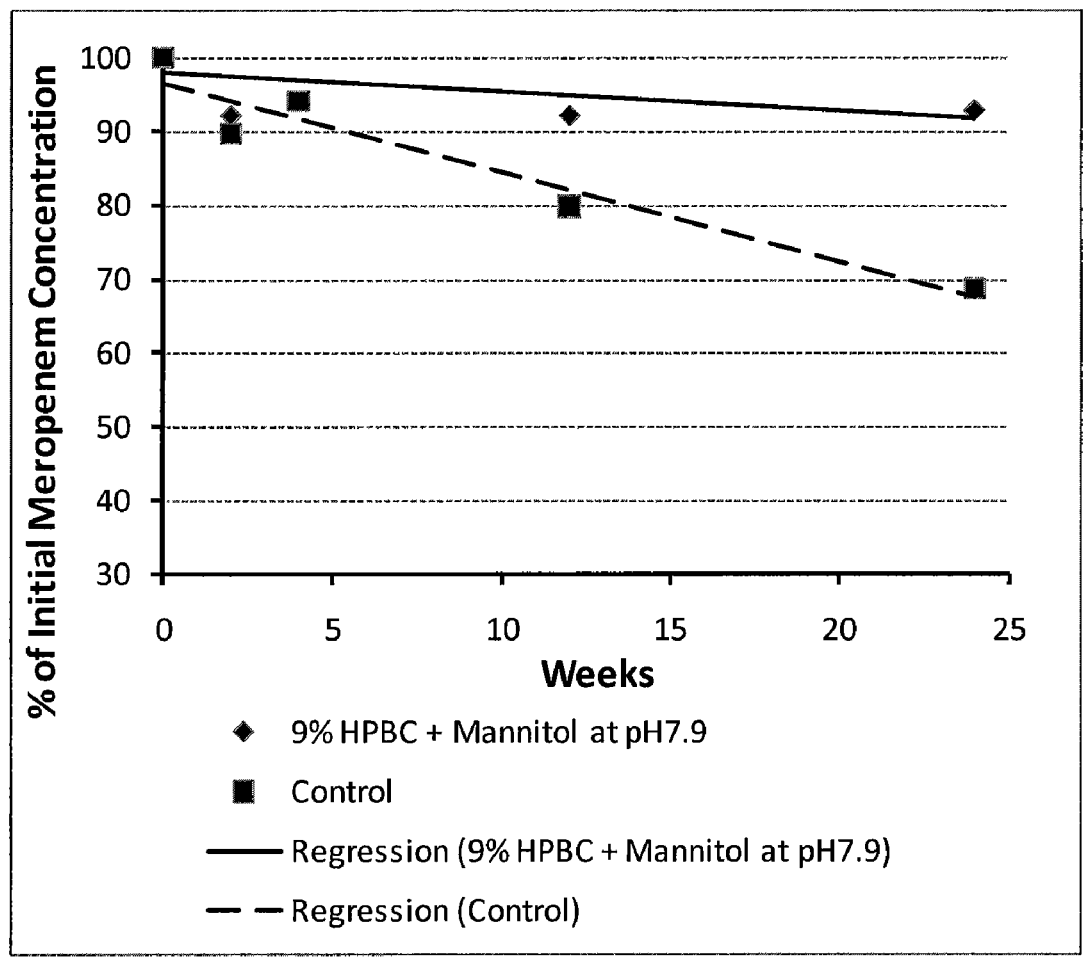
FIG. 8A is a graph showing the percent of initial drug with 9% 2-hydroxypropyl beta-cyclodextrin and mannitol versus storage period (weeks) at −25° C.
Figure 8B:
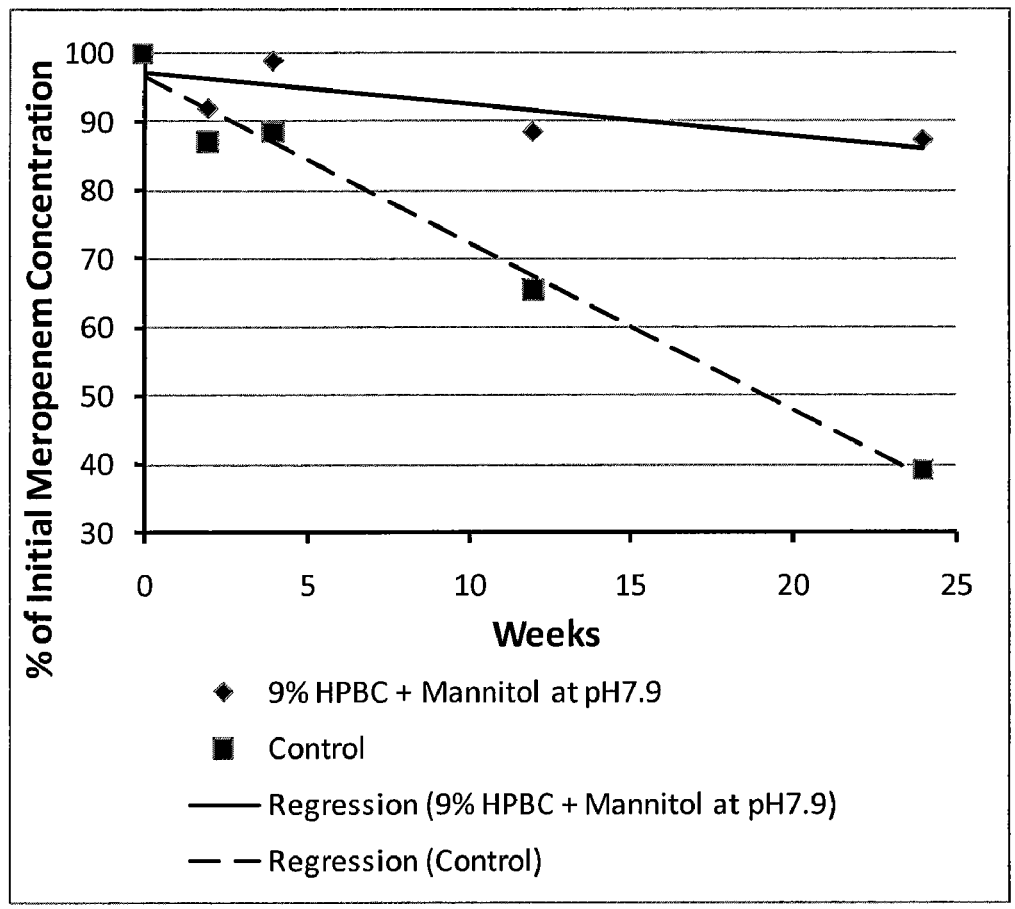
FIG. 8B is a graph showing the percent of initial drug with 9% 2-hydroxypropyl beta-cyclodextrin and mannitol versus storage period (weeks) at −20° C.
Figure 9A:
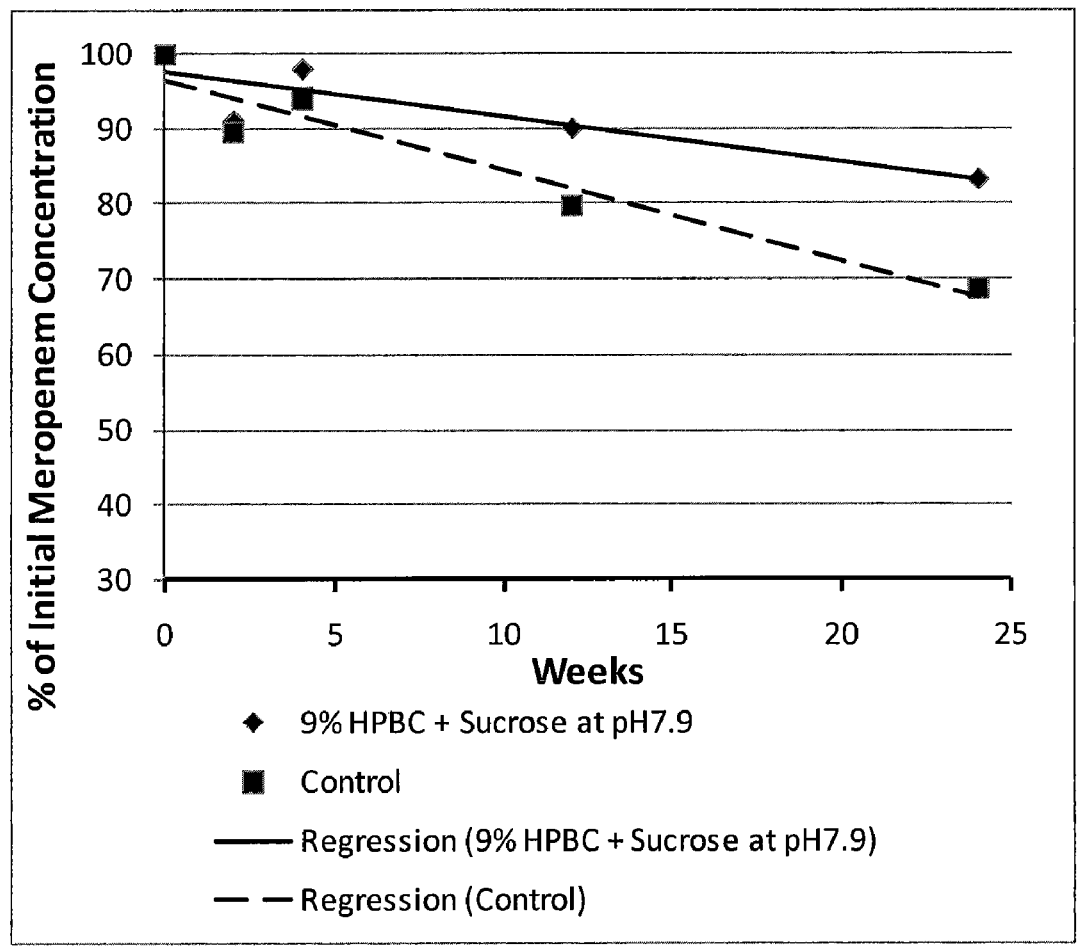
FIG. 9A is a graph showing the percent of initial drug with 9% 2-hydroxypropyl beta-cyclodextrin and sucrose versus storage period (weeks) at −25° C.
Figure 9B:
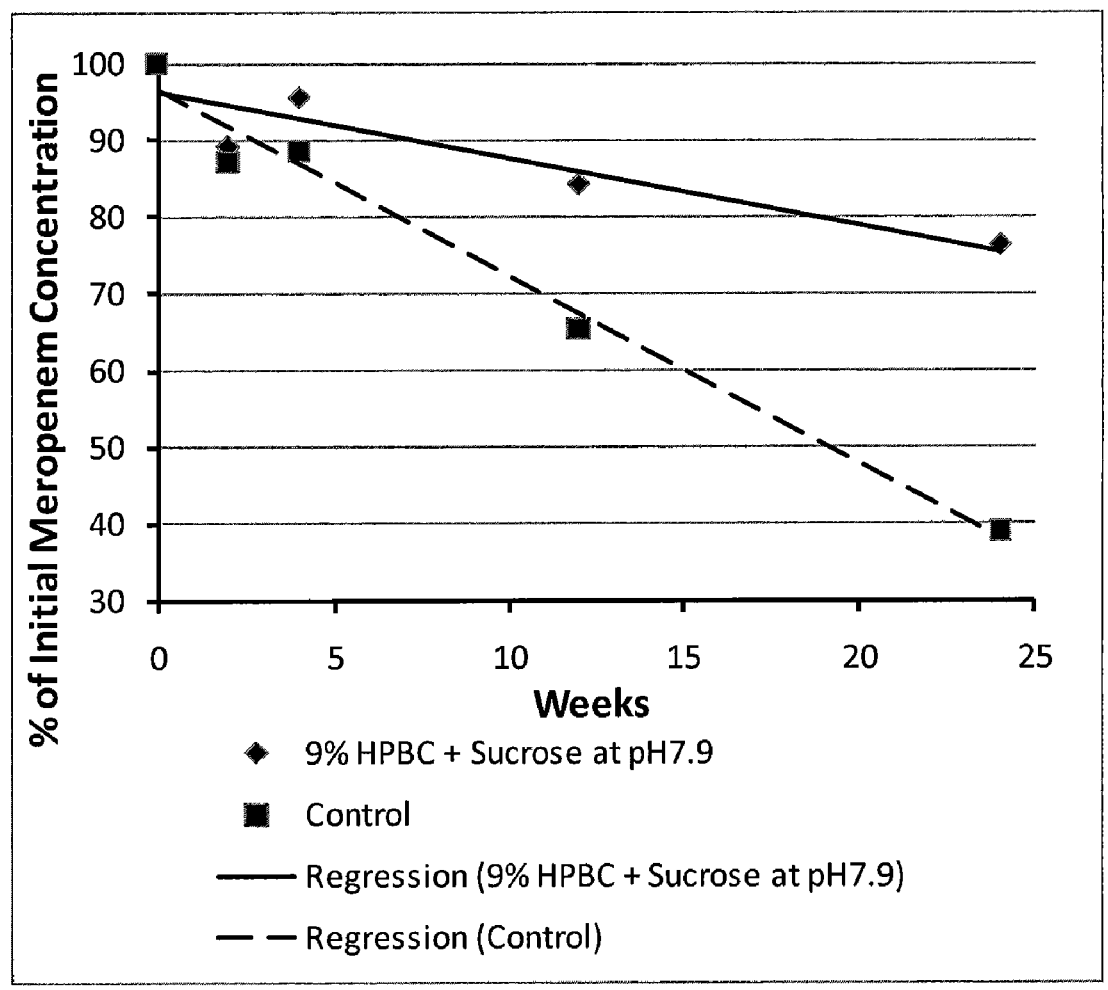
FIG. 9B is a graph showing the percent of initial drug with 9% 2-hydroxypropyl beta-cyclodextrin and sucrose versus storage period (weeks) at −20° C.

Results for Formulation 3C (9% 2-Hydroxypropyl beta-cyclodextrin+mannitol):
    The concentration was also maintained above 90% when stored through 6 months at −25° C. (FIG. 8A).

Results for Formulation 3D (9% 2-Hydroxypropyl beta-cyclodextrin+sucrose):
    The combination of 9% 2-Hydroxypropyl beta-cyclodextrin and sucrose at 4% level may not be sufficient to stabilize the meropenem frozen premix.

Formulations 3A through 3D all showed less drug degradation than the control with 0.9% saline, which showed 12.3% drug loss after one month and 10% loss after approximately 3 weeks (24.3 days).

Example 4

Preparation of a Drug Concentrate with Vitrifying Agent

The following formulation is prepared by mixing the ingredients shown below in a refrigerated vessel (2-8° C.). The drug (1 g) is slowly added per 100 mL of distilled water, resulting in a final concentration of 10 mg/mL drug. The concentrations of all solutes are four-fold higher than in the final solution that is administered to the patient. Flexible plastic containers (100-mL, Baxter PL2040, Galaxy) are filled with the above concentrate (25-mL fill volume) and quickly frozen by placement in a freezer at −20° C. or lower. Optionally, any plastic container can be used that can withstand expansion as the aqueous solution is frozen and is physically rugged at the desired storage temperature.

| Drug: | 10 mg/mL |
|---|---|
| Vitrifying agent: | 5 g dextrose monohydrate |
| Buffer: | 10 mM phosphate |
| pH target: | 7.0 |

One bag (containing 25 mg drug in 25 mL diluent) is thawed at the time of use, and diluted with Sterile Water for Injection USP to a final volume of 100 mL by injecting 75 mL of Sterile Water for Injection through the bag port. The contents are mixed and the final solution is administered to the mammalian subject.

It should be understood that various changes and modifications to the presently preferred embodiments described herein will be apparent to those skilled in the art. Such changes and modifications can be made without departing from the scope of the present subject matter and without diminishing its intended advantages. It is therefore intended that all such changes and modifications be covered by the appended claims.

The invention is claimed as follows:

1. A method of stabilizing a pharmaceutical agent without lyophilization, the method comprising:
   combining a carbapenem with water and a cyclodextrin to form an aqueous carbapenem solution, the cyclodextrin being present in an amount ranging from about 1% to about 30% effective to enhance the formation of an amorphous solid of the aqueous carbapenem solution when the aqueous carbapenem solution is cooled to a temperature below a glass transition temperature of the aqueous carbapenem solution; and
   cooling the aqueous carbapenem solution to a temperature of about −25° C. to about −10° C. to form the amorphous solid of the aqueous carbapenem solution.

2. The method of claim 1 further comprising aseptically filling the aqueous carbapenem solution in a container before cooling.

3. The method of claim 1 further comprising storing the cooled aqueous carbapenem solution at a temperature of about −10° C. to about −25° C. for a period of at least about three months.

4. The method of claim 3 wherein the storing period is at least about six months.

5. The method of claim 3, wherein the carbapenem in the aqueous carbapenem solution exhibits less than about ten percent degradation after storing.

6. The method of claim 3 further comprising thawing the aqueous carbapenem solution and administering the thawed aqueous carbapenem solution to a patient.

7. The method of claim 6 further comprising the step of diluting the thawed carbapenem solution before administering the solution to a patient.

8. The method of claim 1, wherein the carbapenem is unstable in aqueous solution at room temperature.

9. The method of claim 1, wherein the cyclodextrin is 2-hydroxypropyl-beta-cyclodextrin.

10. The method of claim 1, wherein the solution is ready to use upon thawing.

11. The method of claim 1, wherein the solution is a concentrate.

12. The method of claim 11, further comprising the step of diluting the concentrate to provide a solution suitable for infusion into a patient.

* * * * *